United States Patent
Hofmann

Patent Number: 5,871,543
Date of Patent: Feb. 16, 1999

[54] TIBIAL PROSTHESIS WITH MOBILE BEARING MEMBER

[76] Inventor: Aaron A. Hofmann, 6244 S. Ashbury La., Salt Lake City, Utah 84121

[21] Appl. No.: 803,537

[22] Filed: Feb. 20, 1997

Related U.S. Application Data

[60] Provisional application No. 60/012,172 Feb. 23, 1996.

[51] Int. Cl.$^6$ ....................................................... A61F 2/38
[52] U.S. Cl. .................................................................. 623/20
[58] Field of Search .................................... 623/18, 20, 16

[56] References Cited

U.S. PATENT DOCUMENTS

| | | |
|---|---|---|
| 4,136,405 | 1/1979 | Pastrick et al. . |
| 4,216,549 | 8/1980 | Hillbery et al. . |
| 4,219,893 | 9/1980 | Noiles . |
| 4,301,553 | 11/1981 | Noiles . |
| 4,353,136 | 10/1982 | Polyzoides et al. ....................... 623/20 |
| 4,586,933 | 5/1986 | Shoji et al. ................................ 623/20 |
| 4,728,332 | 3/1988 | Albrektsson .............................. 623/20 |
| 4,883,488 | 11/1989 | Bloebaum et al. ....................... 623/20 |
| 4,950,297 | 8/1990 | Elloy et al. ............................... 623/20 |
| 5,071,438 | 12/1991 | Jones et al. ............................... 623/20 |
| 5,116,375 | 5/1992 | Hofmann . |

*Primary Examiner*—Debra S. Brittingham
*Attorney, Agent, or Firm*—Kelly Bauersfeld Lowry & Kelley, LLP.

[57] ABSTRACT

An improved tibial prosthesis is provided for a prosthetic knee wherein the tibial prosthesis includes a mobile bearing member designed to better accommodate a natural range of flex knee motion and force loads applied to the knee joint. The improved tibial prosthesis comprises a tibial component defining a support tray for receiving and supporting a bearing member which in turn defines upwardly presented medial and lateral condylar recesses for respective seated engagement with medial and lateral condyles of a femoral prosthesis. A short lock rim of part-circular shape projects upwardly from the periphery of the tibial support tray, at the medial end thereof, to engage and constrain the bearing member for rotation within the lock rim through a short arcuate path of motion relative to a center axis defined by the geometry of the lock rim, thereby permitting a small degree of anterior-posterior movement of the bearing member lateral end relative to the tibial tray. The range of permissible bearing member displacement can be limited by a stop post projecting upwardly from the tibial tray and received into an elongated guide slot formed in the bearing member.

20 Claims, 4 Drawing Sheets

TIBIAL PROSTHESIS WITH MOBILE BEARING MEMBER

BACKGROUND OF THE INVENTION

This is a Provisional Application Ser. No. 60/012,172 filed Feb. 23, 1996.

This invention relates generally to improvements in prosthetic devices used for reconstruction of the human knee joint. More particularly, this invention relates to an improved tibial prosthesis for a prosthetic knee, including a mobile bearing component adapted to better accommodate a natural range of flex knee motion and force loads applied to the knee joint.

Prosthetic knee joints are generally known in the art and typically comprise matingly configured tibial and femoral prostheses adapted respectively for implantation onto the upper end of a resected tibia and the lower end of a resected femur. The tibial prosthesis incorporates a plastic meniscal bearing member which defines upwardly presented medial and lateral condylar recesses for respective seated engagement of convexly curved medial and lateral condyles on the femoral component. In this regard, the overall geometry of the tibial and femoral prostheses, particularly with respect to the condylar recesses and related femoral condyles, generally resembles the physiology of the natural human knee joint. Desirably, the femoral condyles are retained in seated bearing engagement with the meniscal bearing member throughout a range of natural knee flexion and loading by means of the natural connective tissues including the ligament and tendon structures of the knee joint.

However, the complex mechanical structure of the human knee joint has made it extremely difficult to design an optimum prosthetic joint. More specifically, within a normal range of knee flexion, the natural knee encounters a combination of rolling and sliding motion such that the pivot axis and related contact points between the femur and tibia shift with the degree of knee flexion. This complex motion has made it extremely difficult to design an optimum prosthetic knee capable of emulating natural knee motion while withstanding the relatively high force loads to which the knee joint can be subjected.

One approach for a purportedly improved knee prosthesis involves mounting of the tibial bearing member to permit at least some shifting movement thereof relative to the tibial component which is anchored to patient bone. See, for example, U.S. Pat. No. 5,071,438. This concept involves a pin or post projecting downwardly from the bearing member, at a location beneath the medial condylar recess, for reception into a shallow recess formed in the tibial component. The post and recess are designed to permit a degree of anterior-posterior displacement of the bearing member, relative to the tibial component, to better accommodate natural knee motion with minimum bearing component wear. Unfortunately, however, this concept has suffered from an unacceptable frequency of dislocation and thus has not achieved any widespread acceptance or use.

The present invention pertains to an improved tibial prosthesis of the type having a mobile bearing component, but wherein the mobile bearing component is mounted and constrained in a manner that reduces the likelihood of undesirable dislocation of the prosthesis components.

SUMMARY OF THE INVENTION

In accordance with the invention, an improved tibial prosthesis is provided for a prosthetic knee joint, wherein the tibial prosthesis comprises a tibial component adapted for secure and stable fixation to patient bone, in combination with a mobile meniscal bearing member of suitable high density plastic or the like.

More particularly, the tibial component includes a suitable base surface for attachment to a surgically resected end of the patient's tibia. The attachment is achieved, in the preferred form, by a combination of mechanically interlocking posts and pins, and/or the use of the porous bone ingrowth surfaces. If desired, bone cement may be used to secure the tibial component to patient bone. The tibial component defines an upwardly presented tibial tray for receiving and supporting the meniscal bearing member which in turn defines upwardly presented medial and lateral condylar recesses for respective seated engagement with medial and lateral condyles formed on a femoral component of the prosthetic joint.

In accordance with the invention, the medial end of the tibial tray includes a short upstanding peripheral lock rim of part-circular shape, extending through an arcuate path sufficiently greater than 180 degrees to engage and constrain a medial end of the bearing member. In this regard, the bearing member medial end has a cylindrical segment for rotatable support within the lock rim, to accommodate anterior-posterior shifting movement of the bearing member lateral end relative to a central axis defined by the geometry of the lock rim.

The range of anterior-posterior shifting movement of the bearing member can be limited by a stop post projecting upwardly from the tibial tray for reception into an elongated guide slot formed in the bearing member. In the preferred form, the stop post is disposed generally centrally on the tibial tray and the guide slot is formed in the underside of the bearing member at a location between the medial and lateral condylar recesses. The guide slot may have an arcuate configuration to accommodate anterior-posterior shifting movement of the bearing member through a total range of motion on the order of about 20 degrees.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
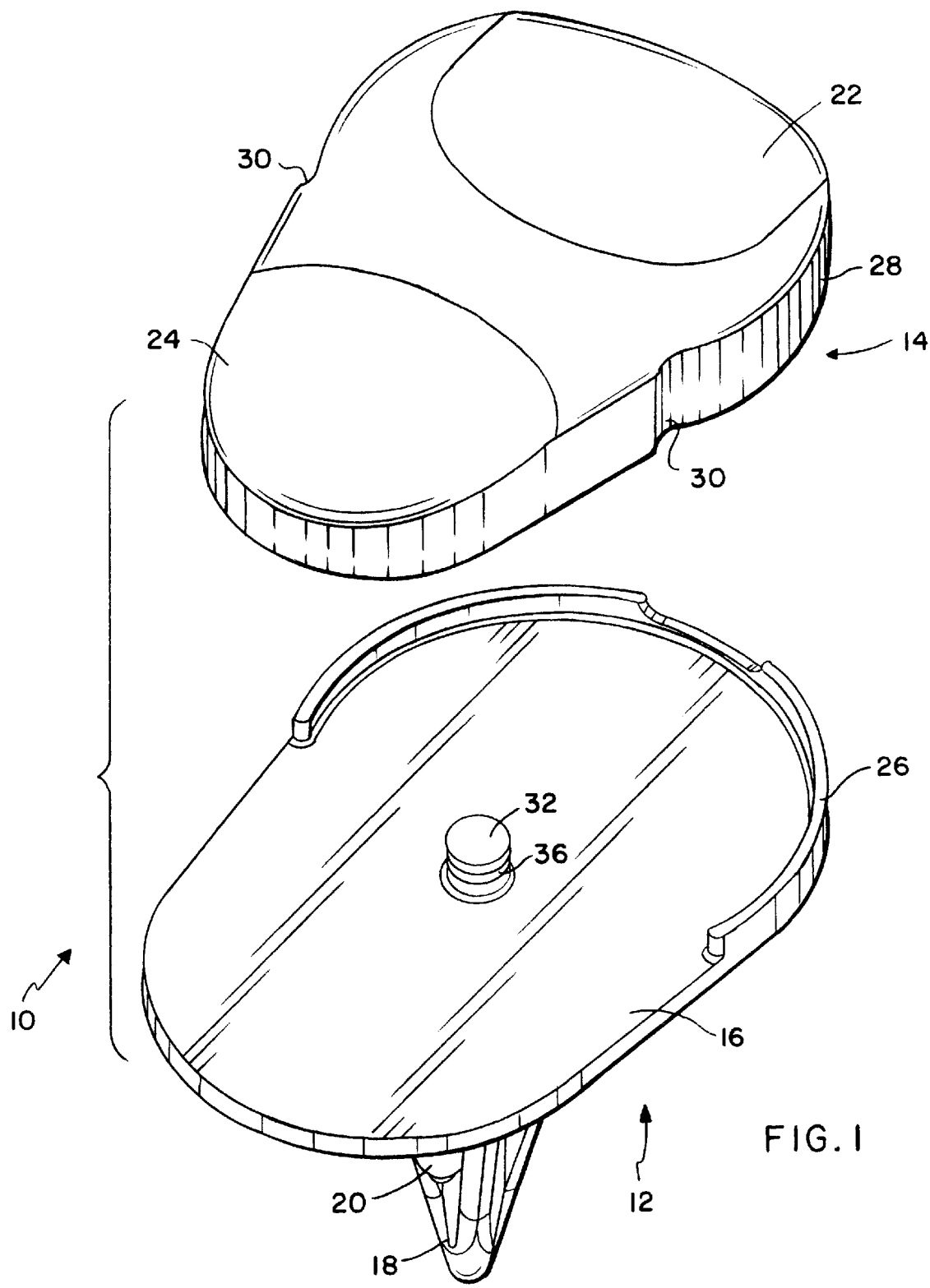
FIG. 1 is an exploded perspective view illustrating the improved tibial prosthesis embodying the novel features of the invention.
Figure 2:
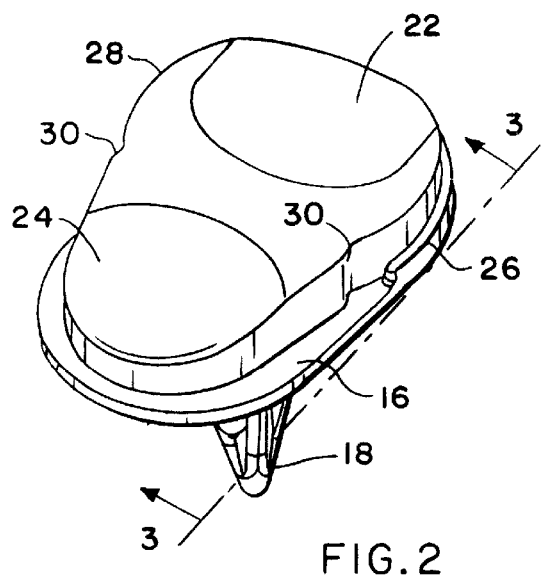
FIG. 2 is a perspective view, not in exploded form, of the tibial prosthesis shown in FIG. 1.

As shown in the exemplary drawings, a tibial prosthesis for a prosthetic knee is referred to generally in FIG. 1 by the reference numeral 10. The tibial prosthesis 10 generally comprises a tibial component 12 adapted for secure and stable fixation onto the upper end of a patient's resected tibia (not shown), in combination with a bearing member 14. The bearing member 14 is supported by the tibial component 12 in a mobile manner, to permit limited shifting movement of the bearing member 14 relative to the tibial component 12 to better accommodate a natural range of flex knee motion and force loads applied to the reconstructed knee joint. In this regard, the improved tibial prosthesis 10 of the present invention represents an improvement over U.S. Pat. No. 5,071,438, which is incorporated by reference herein.

The tibial component 12 is constructed, in most respects, to have a generally conventional configuration for secure mounting onto the patient's tibia in the course of knee reconstruction surgery. In this regard, the tibial component 12 is constructed from a strong and biocompatible surgical implant material, such as cobalt chrome or titanium alloy or the like. As shown best in FIGS. 1–3 and 5–7, the tibial component 12 provides an upper plateau or tray 16 with a central tapered anchoring or fixation post 18 projecting downwardly therefrom. In addition, one or more antirotation pins or flutes 20 may also be provided to project downwardly from the underside of the tibial tray 16. The fixation post 18 and antirotation pins 20 provide a means for a secure mechanical interlock with prepared patient bone (not shown), and these mechanical interlock structures may be used in combination with porous bone ingrowth surfaces (not shown) or the use of bone cement for securely attaching the tibial component 12 to patient bone.

The tibial tray 16 has a conventional geometry to define a generally circular medial end merging integrally with a generally circular lateral end of somewhat smaller diametric size, resulting in an overall tray configuration of roughly elliptical appearance. The tray 16 is designed to receive and support the bearing member 14, formed typically from a high density and biocompatible plastic material such as polyethylene or the like, and having a shape roughly conforming to the geometry of the tibial tray. As shown best in FIGS. 1, 2 and 4, the bearing member 14 defines an upwardly presented medial condylar recess 22 and a lateral condylar recess 24 disposed respectively above the medial and lateral ends of the tibial tray 16, and positioned for respective seated engagement of medial and lateral condyles (not shown) of a femoral component as is known in the art.

Figure 4:
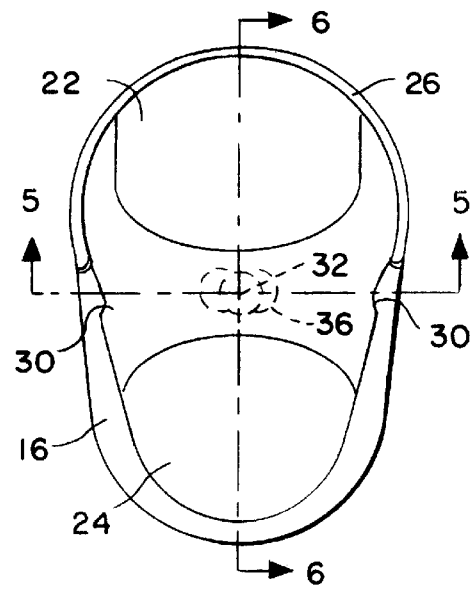
FIG. 4 is a top plan view of the tibial prosthesis shown in FIG. 2.
Figure 3:
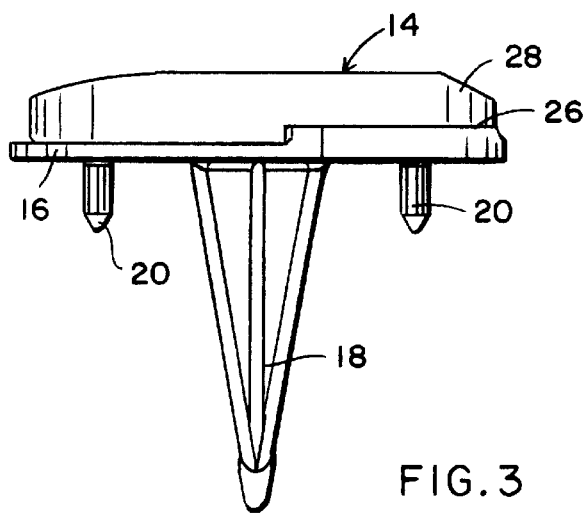
FIG. 3 is a side elevation view taken generally on the line 3—3 of FIG. 2.
Figure 5:
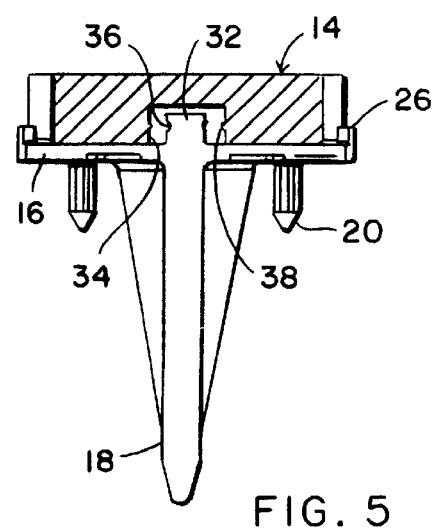
FIG. 5 is a transverse vertical sectional view taken generally on the line 5—5 of FIG. 4.
Figure 6:
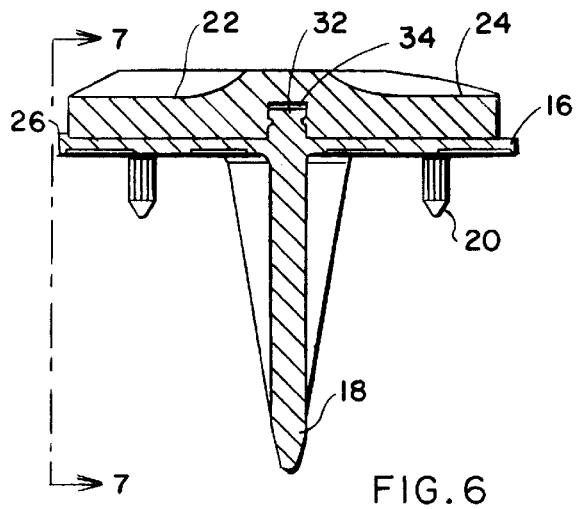
FIG. 6 is a longitudinal vertical sectional view taken generally on the line 6—6 of FIG. 4.
Figure 7:
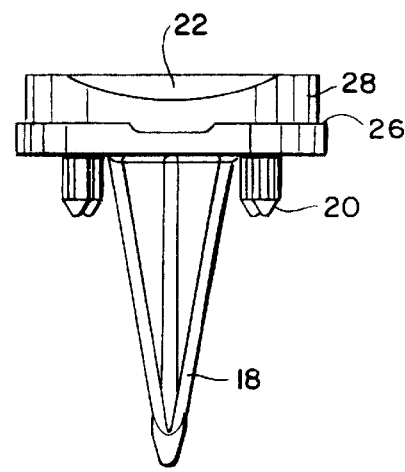
FIG. 7 is a rear elevational view taken generally on the line 7—7 of FIG. 6.
Figure 8:
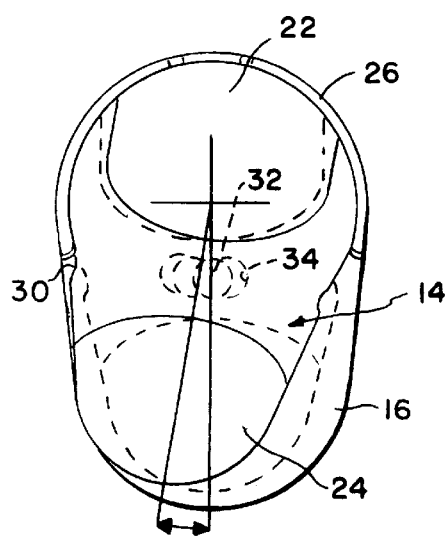
FIGS. 8 and 9 are top plan views similar to FIG. 4 but illustrating anterior-posterior shifting movement of a bearing member relative to a tibial component.
Figure 9:
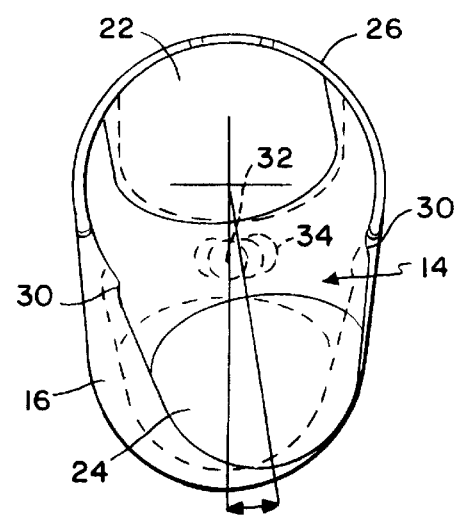

In accordance with the present invention, the tibial tray 16 additionally includes a short upstanding lock rim 26 extending with a part-circular configuration about the periphery of the tray medial end. In this regard, the lock rim 26 is formed on a radial center to receive and rotatably support a matingly shaped cylindrical medial end segment 28 of the bearing member 14. FIG. 4 shows the lock rim 26 extending through a sufficient circular arc greater than 180 degrees to capture and constrain the cylindrical medial end segment 28 of the bearing member 14 for rotatable movement relative to a center axis defined by the lock rim, and further wherein the cylindrical segment 28 of the bearing member 14 extends through a part-circular path sufficiently greater than the lock rim 26 to accommodate anterior-posterior displacement of the bearing member lateral end as the medial end rotates within the lock rim. FIG. 4 shows a pair of stop lands 30 formed on the bearing member 14 in the transition region between the medial and lateral ends, wherein these stop lands 30 are disposed to engage the adjacent ends of the lock rim 26 (FIGS. 8 and 9) to define end limits to the permitted anterior-posterior displacement of the bearing member relative to the tibial tray 16. FIGS. 8 and 9 also show the center axis of the lock rim 26 offset to one side of a central axis of the tibial component (i.e., to one side of the post 18). Although not shown in the drawings, it will be understood that the rim 26 may extend entirely around the periphery of the tibial tray inclusive of the lateral end thereof, or to include at least a portion of the lateral end, for improved structural strength of the tibial tray and/or an additional stop to limit excessive anterior-posterior displacement of the bearing member.

During normal use of the tibial prosthesis subsequent to the reconstructive knee surgery in a patient, the bearing member 14 engages and supports the femoral condyles on the femoral component (not shown) of a prosthetic knee joint. As the patient's knee is moved through a normal range of motion, the femoral condyles pivot and slide relative to the bearing condylar recesses 22, 24. Natural knee flexion is accommodated by the mobile bearing member 14 of the present invention, since forces interacting between the femoral component and the bearing member can result in a small degree of anterior or posterior shifting of the lateral end of the bearing member, within the limits of rotation defined by the lock rim 26 and the adjacent stop lands 30 on the bearing member.

In accordance with a further aspect of the invention, a stop post 32 is also provided on the tibial component 12 to help guard against inadvertent and undesirable dislocation of the prosthesis structures during normal knee movements. The stop post 32 is shown to project upwardly from the tibial tray 16, at a generally centered position shown to be in coaxial alignment with the underlying fixation post 18. The stop post 32 projects upwardly into a guide slot 34 formed in the underside of the bearing member 14. In the preferred geometry, the guide slot 34 has an arcuate shape (FIGS. 4, 8 and 9) to guide and constrain the bearing member 14 for movement through a limited path. In a preferred configuration, anterior shifting is limited to a range of about 10 degrees, and posterior shifting is similarly limited to a range of about 10 degrees, for a total range of motion of about 20 degrees, as viewed in FIGS. 8 and 9. The stop post 32 conveniently includes a peripheral groove 36 for snap-fit reception of a bead 38 (FIG. 5) lining the guide slot 34 to vertically lock the bearing member 14 in place onto the tibial tray 16.

Figure 10:
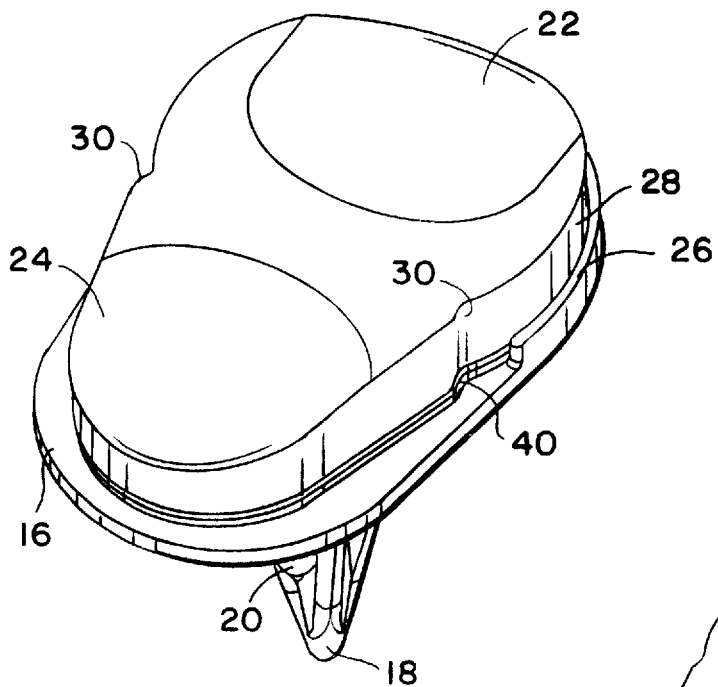
FIG. 10 is a perspective view similar to FIG. 2, but illustrating an alternative preferred form of the invention.
Figure 11:
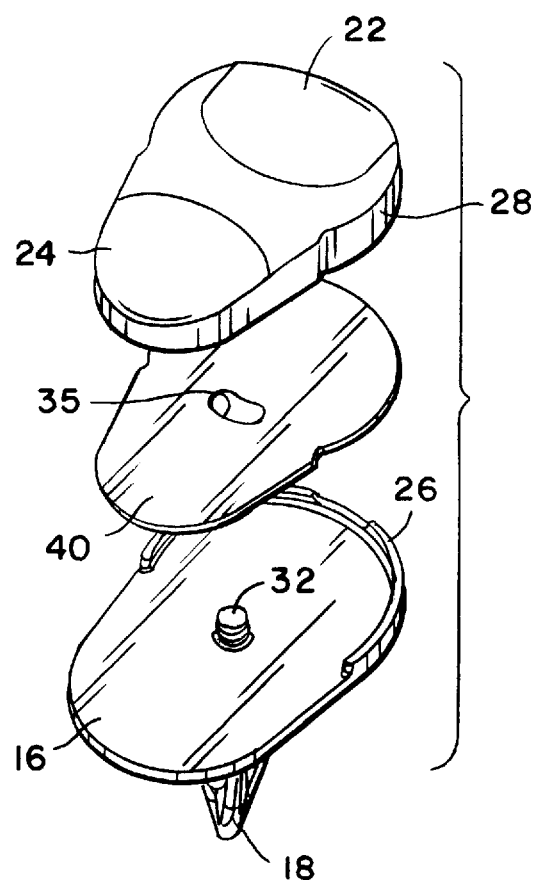
FIG. 11 is an exploded perspective view of the embodiment of FIG. 10.

FIGS. 10 and 11 illustrate an alternative preferred form of the invention, wherein components identical to those shown and described in FIGS. 1–9 are depicted by the same reference numerals. The embodiment of FIGS. 10 and 11 differs from the embodiment of FIGS. 1–9 by the inclusion of a base plate 40 attached in a suitable manner to the underside of the bearing member 14. For example, the base plate 40 may include short upstanding posts (not shown) for reception into mating sockets (also not shown) formed in the underside of the bearing member. The base plate 40 has a geometry conforming to the outline shape of the bearing member 14, and further include a guide slot 35 therein in alignment with the guide slot 34 (not shown in FIGS. 10 and 11) formed in the underside of the bearing member 14. The base plate 40 is constructed from a suitable implantable metal material so that the sliding surface between the base plate 14 and the tibial tray 16 is a metal-to-metal surface for reducing wear on the non-metal bearing member 14.

A variety of further modifications and improvements to the tibial knee prosthesis described herein are believed to be apparent to those skilled in the art. In this regard, it will be recognized that the geometry of the invention depicted in the illustrative drawings is intended for use in an implant application wherein the patient's posterior cruciate ligament is removed. It will be understood that appropriate reshaping of the knee prosthesis components can be accommodated for an application wherein the posterior cruciate ligament is retained. Accordingly, no limitation on the invention is intended by way of the foregoing description and accompanying drawings, except as set forth in the appended claims.

What is claimed is:

1. A knee joint prosthesis, comprising:
   a tibial component including means for fixation to a resected end of a patient's tibia, said tibial component defining a tibial tray having a medial end and a lateral end, said tibial tray medial end including a short upstanding lock rim of generally cylindrical shape; and
   a meniscal bearing member supported on said tibial tray, said bearing member having a medial end and a lateral end positioned respectively over said tibial tray medial and lateral ends and further defining medial and lateral condylar recesses, said bearing member medial end having a generally cylindrical shape for rotatable support within said tibial tray lock rim to permit anterior-posterior shifting of said bearing member lateral end relative to a central axis defined by said lock rim, said central axis of said lock rim being offset from a central axis of said tibial component.

2. The knee joint prosthesis of claim 1 wherein said lock rim extends through an arcuate path of at least about 180 degrees.

3. The knee joint prosthesis of claim 1 wherein said lock rim extends through an arcuate path of greater that 180 degrees sufficient to engage and retain said bearing member medial end.

4. The knee joint prosthesis of claim 3 wherein said bearing member medial end has a cylindrical shape extending through an arcuate path greater than the arcuate path defined by said tibial tray medial end.

5. The knee joint prosthesis of claim 1 further including stop means for limiting the range of anterior-posterior movement of said bearing member lateral end.

6. The knee joint prosthesis of claim 5 wherein said stop means comprises a stop post formed on one of said tibial component and said bearing member, and a guide slot formed on the other of said tibial component and said bearing member and extending generally in an anterior-posterior direction, said stop post being received into said guide slot whereby said guide slot limits the range of anterior-posterior movement of said bearing member lateral end.

7. The knee prosthesis of claim 6 wherein said guide slot has an arcuate shape.

8. The knee prosthesis of claim 7 wherein said guide slot extends through an arcuate path of about 20 degrees.

9. The knee prosthesis of claim 6 further including means for retaining said stop post within said guide slot.

10. The knee prosthesis of claim 9 wherein said retaining means comprises a snap fit interconnection.

11. The knee prosthesis of claim 6 wherein said stop post is formed to project upwardly from said tibial tray, and wherein said guide slot is formed in an underside of said bearing member.

12. The knee prosthesis of claim 5 wherein said stop means comprises a pair of stop lands formed on said bearing member for respectively engaging opposite ends of said lock rim upon anterior-posterior movement of said bearing member lateral end to the respective opposite ends of an range of motion.

13. The knee prosthesis of claim 1 further including a slide plate interposed between said tibial tray and said bearing member, said slide plate being formed from a metal material and being movable with said bearing member.

14. The knee joint prosthesis of claim 1 wherein said lock rim engages and constrains said bearing member medial end against substantial anterior-posterior shifting in response to rotation of said bearing member medial end within said lock rim.

15. A knee prosthesis, comprising:
   a tibial component including means for fixation to an resected end of a patient's tibia, said tibial component defining a tibial tray having a medial end and a lateral end, said medial end having a generally cylindrical shape and including a short upstanding lock rim of generally part-circle shape extending through an arcuate path greater that 180 degrees; and
   a meniscal bearing member supported on said tibial tray, said bearing member defining a medial end and a lateral end supported respectively over said tibial tray medial and lateral ends, said bearing member medial end defining a cylindrical surface extending through an arcuate path greater than said lock rim, and said lock rim engaging and retaining said cylindrical surface of said bearing member medial end for rotational movement about a central axis defined by said lock rim to permit anterior-posterior movement of said bearing member lateral end;
   said tibial tray and said bearing member further including stop means for limiting a permitted range of anterior-posterior movement of said bearing member lateral end.

16. The knee prosthesis of claim 15 wherein said stop means comprises a stop post formed on one of said tibial component and said bearing member, and a guide slot formed on the other of said tibial component and said bearing member and extending generally in an anterior-posterior direction, said stop post being received into said guide slot whereby said guide slot limits a range of anterior-posterior movement of said bearing member lateral end.

17. The knee prosthesis of claim 16 wherein said guide slot has an arcuate shape.

18. The knee prosthesis of claim 16 further including snap fit means for retaining said stop post within said guide slot.

19. The knee prosthesis of claim 15 wherein said stop means comprises a pair of stop lands formed on said bearing member for respectively engaging opposite ends of said lock rim upon anterior-posterior movement of said bearing member lateral end to the respective opposite ends of the permitted range of motion.

20. The knee prosthesis of claim 15 further including a slide plate interposed between said tibial tray and said bearing member, said slide plate being formed from a metal material and being movable with said bearing member.

* * * * *